US009555072B2

(12) United States Patent
Johnson et al.

(10) Patent No.: US 9,555,072 B2
(45) Date of Patent: Jan. 31, 2017

(54) VIRAL VECTORS AND THEIR USE IN THERAPEUTIC METHODS

(71) Applicants: Catherex, Inc., Bala Cynwyd, PA (US); The General Hospital Corporation, Boston, MA (US); Georgetown University, Washington, DC (US)

(72) Inventors: Paul Johnson, Vancouver (CA); Robert L. Martuza, Cambridge, MA (US); Samuel D. Rabkin, Swampscott, MA (US); Tomoki Todo, Belmont, MA (US)

(73) Assignees: The General Hospital Corporation, Boston, MA (US); Georgetown University, Washington, DC (US); Catherex, Inc., Dover, DE (US)

( * ) Notice: Subject to any disclaimer, the term of this patent is extended or adjusted under 35 U.S.C. 154(b) by 0 days.

(21) Appl. No.: 14/524,163

(22) Filed: Oct. 27, 2014

(65) Prior Publication Data
US 2015/0071965 A1 Mar. 12, 2015

Related U.S. Application Data

(60) Continuation of application No. 13/924,936, filed on Jun. 24, 2013, now Pat. No. 8,871,193, which is a division of application No. 12/721,599, filed on Mar. 11, 2010, now Pat. No. 8,470,577, which is a continuation of application No. 10/107,036, filed on Mar. 27, 2002, now Pat. No. 7,749,745.

(60) Provisional application No. 60/279,069, filed on Mar. 27, 2001.

(51) Int. Cl.
| | |
|---|---|
| *A61K 38/16* | (2006.01) |
| *C12N 15/86* | (2006.01) |
| *A61K 35/763* | (2015.01) |
| *A61K 35/768* | (2015.01) |
| *C12N 7/00* | (2006.01) |
| *A61K 48/00* | (2006.01) |
| *A61K 39/00* | (2006.01) |

(52) U.S. Cl.
CPC ........... *A61K 38/162* (2013.01); *A61K 35/763* (2013.01); *A61K 35/768* (2013.01); *C12N 7/00* (2013.01); *C12N 15/86* (2013.01); *A61K 48/00* (2013.01); *A61K 2039/53* (2013.01); *C12N 2710/16632* (2013.01); *C12N 2710/16634* (2013.01); *C12N 2710/16643* (2013.01); *C12N 2710/16671* (2013.01)

(58) Field of Classification Search
None
See application file for complete search history.

(56) References Cited

U.S. PATENT DOCUMENTS

| | | | |
|---|---|---|---|
| 5,750,398 A | 5/1998 | Johnson et al. | |
| 5,824,318 A | 10/1998 | Mohr et al. | |
| 6,248,320 B1 | 6/2001 | Coffin et al. | |
| 6,261,552 B1 | 7/2001 | DeLuca | |
| 7,223,593 B2 * | 5/2007 | Coffin | A61K 35/763 |
| | | | 424/93.2 |
| 7,749,745 B2 | 7/2010 | Johnson et al. | |
| 2003/0228281 A1 | 12/2003 | Fong et al. | |

FOREIGN PATENT DOCUMENTS

| | | |
|---|---|---|
| EP | 0 453 242 A1 | 10/1991 |
| EP | 1 252 322 | 11/2004 |
| WO | 92/13943 | 8/1992 |
| WO | 96/00007 | 1/1996 |
| WO | 96/03997 | 2/1996 |
| WO | 96/39841 | 12/1996 |
| WO | 99/07394 | 2/1999 |
| WO | WO 01/53505 | 7/2001 |
| WO | WO 01/53506 | 7/2001 |

OTHER PUBLICATIONS

Kinoshita et al., Neurologia medico-chirurgica vol. 44 (2004) No. 12 pp. 669-673.*
"Amgen Announces Top-Line Results of Phase 3 Talimogene Laherparepvec Trial in Melanoma," Amgen News Releases, dated Mar. 19, 2013. Accessed at: http://www.amgen.com/media/media_pr_detail.jsp?year=2013&releaseID=1798143.
"Amgen Provides Update on Phase 3 Study of Talimogene Laherparepvec in Patients With Metastatic Melanoma," Amgen News Releases, dated Apr. 4, 2014. Accessed at: http://www.amgen.com/media/media_pr_detail.jsp?year=2014&releaseID=1915897.
Cassady et al., "The Herpes Simplex Virus $U_s11$ Protein Effectively Compensates for the $_{\gamma 1}34.5$ Gene if Present before Activation of Protein Kinase R by Precluding Its Phosphorylation and That of the αSubunit of Eukaryotic Translation Initiation Factor 2," J. Virol. 72:8620-8626, 1998.
Cassady et al., "The Second-Site Mutation in the Herpes Simplex Virus Recombinants Lacking the $_{\gamma 1}34.5$ Genes Precludes Shutoff of Protein Synthesis by Blocking the Phosphorylation of eIF-2α," J. Virol. 72:7005-7011, 1998.
Chambers et al., "Comparison of Genetically Engineered Herpes Simplex Viruses for the Treatment of Brain Tumors in a scid Mouse Model of Human Malignant Glioma," Proc. Natl. Acad. Sci. U.S.A. 92:1411-1415, 1995.
Chou et al., "The $_{\gamma 1}34.5$ Gene of Herpes Simplex Virus 1 Precludes Neuroblastoma Cells from Triggering Total Shutoff of Protein Synthesis Characteristic of Programmed Cell Death in Neuronal Cells," Proc. Natl. Acad. Sci. U.S.A. 89:3266-3270, 1992.
Gelman et al., "Herpes Simplex Virus Immediate-Early Promoters are Responsive to Virus and Cell trans-Acting Factors," J. Virol. 61:2286-2296, 1987.
Goldstein et al., "Herpes Simplex Virus Type 1-Induced Ribonucleotide Reductase Activity Is Dispensable for Virus Growth and DNA Synthesis: Isolation and Characterization of an ICP6 IacZ Insertion Mutant," J. Virol. 62:196-205, 1988.

(Continued)

Primary Examiner — Shanon A Foley
Assistant Examiner — Myron Hill
(74) Attorney, Agent, or Firm — Fish & Richardson P.C.

(57) ABSTRACT

The invention provides viral vectors (e.g., herpes viral vectors) and methods of using these vectors to treat disease.

19 Claims, 7 Drawing Sheets

(56) References Cited

OTHER PUBLICATIONS

Greco et al., "The DNA Sequence Coding for the 5' Untranslated Region of Herpes Simplex Virus Type 1 ICP22 mRNA Mediates a High Level of Gene Expression," J. Gen. Virol. 75:1693-1702, 1994.

He et al., "Suppression of the Phenotype of $_{\gamma_1}$34.5⁻ Herpes Simplex Virus 1: Failure of Activated RNA-Dependent Protein Kinase to Shut Off Protein Synthesis is Associated with a Deletion in the Domain of the α47 Gene," J. Virol. 71:6049-6054, 1997.

Hughes et al., "Critical analysis of an oncolytic herpesvirus encoding granulocyte-macrophage colony stimulating factor for the treatment of malignant melanoma," Oncol Virotherapy. 4:11-20 (2014).

Hunter et al., "Attenuated, Replication-Competent Herpes Simplex Virus Type 1 Mutant G207: Safety Evaluation of Intracerebral Injection in Nonhuman Primates," J. Virol. 73:6319-6326, 1999.

Jennings et al., "Effect of Herpes Simplex Virus Types 1 and 2 on Surface Expression of Class I Major Histocompatibility Complex Antigens on Infected Cells," J. Virol. 56:757-766, 1985.

Johnson et al., "Improved Cell Survival by the Reduction of Immediate-Early Gene Expression in Replication-Defective Mutants of Herpes Simplex Virus Type 1 but Not by Mutation of the Virion Host Shutoff Function," J. Virol. 68:6347-6362, 1994.

Krisky et al., "Rapid method for construction of recombinant HSV gene transfer vectors," Gene Ther. 4(10):1120-5 (1997).

Krisky et al., "Development of Herpes Simplex Virus Replication-Defective Multigene Vectors for Combination Gene Therapy Applications," Gene Ther. 5:1517-1530, 1998.

Liu et al., "ICP34.5 Deleted Herpes Simplex Virus with Enhanced Oncolytic, Immune Stimulating, and Anti-Tumor Properties," Gene Ther. 10:292-303, 2003.

Locker et al., "BamI, KpnI, and SalI Restriction Enzyme Maps of the DNAs of Herpes Simplex Virus Strains Justin and F: Occurrence of Heterogeneities in Defined Regions of the Viral DNA," J. Virol. 32(2):429-441, 1979.

Longnecker et al., "Generation of an Inverting Herpes Simplex Virus 1 Mutant Lacking the L-S Junction α Sequences, an Origin of DNA Synthesis, and Several Genes Including Those Specifying Glycoprotein E and the α47 Gene," J. Virol. 58:583-591, 1986.

Martuza, "Conditionally Replicating Herpes Vectors for Cancer Therapy," J. Clin. Invest. 105:841-846, 2000.

Mavromara-Nazos et al., "Construction and Properties of a Variable Herpes Simplex Virus 1 Recombinant Lacking Coding Sequences of the Alpha 47 Gene," J. Virol. 60:807-812, 1986.

McGeoch et al., Genbank Accession No. X14112, Nov. 14, 2006.

Mineta et al., "Attenuated Multi-mutated Herpes Simplex Virus-1 for the Treatment of Malignant Gliomas," Nat. Med. 1:938-943, 1995.

Mohr et al., "A Herpesvirus Genetic Element Which Affects Translation in the Absence of the Viral GADD34 Function," EMBO J. 15:4759-4766, 1996.

Pogue-Geile et al., "Enhanced Rate of Conversion or Recombination of Markers Within a Region of Unique Sequence in the Herpes Simplex Virus Genome," J. Virol. 58:704-708, 1986.

Randazzo et al. J Investigative Dermatol 1997 vol. 108, pp. 953-937.

Schaffer et al., "Herpes Simplex Virus," Genetic Maps 4:93-98, Cold Spring Harbor Laboratories Press, 1987.

Senzer et al., "Phase II clinical trial of a granulocyte-macrophage colony-stimulating factor-encoding, second-generation oncolytic herpesvirus in patients with unresectable metastatic melanoma," J Clin Oncol. 27(24):5763-71 (2009).

Todo et al., "Oncolytic Herpes Simplex Virus Vector with Enhanced MHC Class I Presentation and Tumor Cell Killing," Proc. Natl. Acad. Sci. U.S.A. 98:6396-6401, 2001.

Todo et al., "Viral Shedding and Biodistribution of G207, a Multimutated, Conditionally Replicating Herpes Simplex Virus Type 1, after Intracerebral Inoculation in Aotus," Mol. Ther. 2:588-595, 2000.

Tomazin et al., "Herpes Simplex Virus Type 2 ICP47 Inhibits Human TAP but Not Mouse TAP," J. Virol. 72:2560-2563, 1998.

Varghese et al. Cancer Gene Therapy 2002 vol. 9, pp. 967-978.

Varmuza et al., "Unstable Heterozygosity in a Diploid Region of Herpes Simplex Virus DNA," J. Virol. 49:356-362, 1984.

Voss et al., "Properties of two 5'—Coterminal RNAs Transcribed Part Way and Across the S Component Origin of DNA Synthesis of the Herpes Simplex Virus 1 Genome," Proc. Natl. Acad. Sci. USA 85:8454-8458, 1988.

York et al., "A Cytosolic Herpes Simplex Virus Protein Inhibits Antigen Presentation to CD8⁺ T Lymphocytes," Cell 77:525-535, 1994.

Barba et al., "Development of anti-tumor immunity following thymidine kinase-mediated killing of experimental brain tumors," Proc. Natl. Acad. Sci. USA, 91:4348-4352 (1994).

D'Angelica et al., "In vivo IL-2 gene transfection of implanted tumors with HSV vectors induces a systemic antitumor response," Proceedings of the American Association for Cancer Research, 37:443, #3020 (1996).

Dranoff et al., "Vaccination with irradiated tumor cells engineered to secrete murine granulocyte-macrophage colony-stimulating factor stimulates potent, specific, and long-lasting anti-tumor immunity," Proc. Natl. Acad. Sci. USA, 90:3539-3543 (1993).

Mulvey et al., "A Herpesvirus Ribosome-Associated, RNA-Binding Protein Confers a Growth Advantage upon Mutants Deficient in a GADD34-Related Function," Journal of Virology, 73(4):3375-3385 (1999).

Toda et al., "Intratumoral Inoculation of a replication-competent herpes simplex virus, G207, Induces an antitumor immune response," Proceedings of the American Association for Cancer Research, 38:175-176, #1176 (1997).

\* cited by examiner

VIRAL VECTORS AND THEIR USE IN THERAPEUTIC METHODS

FIELD OF THE INVENTION

This invention relates to viruses and their use in therapeutic methods.

BACKGROUND OF THE INVENTION

The use of replication-competent viral vectors, such as herpes simplex virus type 1 (HSV-1) vectors, is an attractive strategy for tumor therapy, because such viruses can replicate and spread in situ, exhibiting oncolytic activity through direct cytopathic effect (Kirn, J. Clin. Invest. 105:837-839, 2000). A number of oncolytic HSV-1 vectors have been developed that have mutations in genes associated with neurovirulence and/or viral DNA synthesis, in order to restrict replication of these vectors to transformed cells and not cause disease (Martuza, J. Clin. Invest. 105:841-846, 2000).

In designing viral vectors for clinical use, it is essential that ample safeguards be employed. G207 is an oncolytic HSV-1 vector derived from wild-type HSV-1 strain F (Mineta et al., Nat. Med. 1:938-943, 1995). It has deletions in both copies of the major determinant of HSV neurovirulence, the γ34.5 gene, and an inactivating insertion of the *E. coli* lacZ gene in UL39, which encodes the infected-cell protein 6 (ICP6) (Mineta et al., Nat. Med. 1:938-943, 1995). ICP6 is the large subunit of ribonucleotide reductase, a key enzyme for nucleotide metabolism and viral DNA synthesis in non-dividing cells but not dividing cells (Goldstein et al., J. Virol. 62:196-205, 1988). In addition to being the major determinant of HSV neurovirulence (Chou et al., Science 250:1262-1266, 1990), ICP34.5 also functions by blocking host cell induced shutoff of protein synthesis in response to viral infection (Chou et al., Proc. Natl. Acad. Sci. U.S.A. 89:3266-3270, 1992). This is likely responsible for the less efficient growth of γ34.5$^-$ mutants compared to wild-type HSV, which has been observed in many tumor cell types (McKie et al., Br. J. Cancer 74:745-752, 1996; Andreansky et al., Cancer Res. 57:1502-1509, 1997; Chambers et al., Proc. Natl. Acad. Sci. U.S.A. 92:1411-1415, 1995). This double mutation confers important advantages: minimal chance of reverting to wild type, preferential replication in tumor cells, attenuated neurovirulence, and ganciclovir/acyclovir hypersensitivity. G207 effectively kills multiple types of tumor cells in culture and in mice harboring tumors subcutaneously or intracranially (Mineta et al., Nat. Med. 1:938-943, 1995; Yazaki et al., Cancer Res. 55:4752-4756, 1995; Toda et al., Hum. Gene Ther. 9:2177-2185, 1998; Todo et al., Hum. Gene Ther. 10:2741-2755, 1999; Chahlavi et al., Neoplasia 1:162-169, 1999; Kooby et al., FASEB J. 13:1325-1334, 1999; Lee et al., J. Gastrointest. Surg. 3:127-133, 1999). In several syngeneic tumor models in immunocompetent mice, oncolysis caused by intraneoplastic inoculation of G207 elicited a systemic immune response and tumor-specific cytotoxic T lymphocytes (Todo et al., Hum. Gene Ther. 10:2741-2755, 1999; Toda et al., Hum. Gene Ther. 10:385-393, 1999; Todo et al., Hum. Gene Ther. 10:2869-2878, 1999).

G207 has minimal toxicity when injected into the brains of HSV-1-susceptible mice or nonhuman primates (Hunter et al., J. Virol. 73:6319-6326, 1999; Sundaresan et al., J. Virol. 74:3832-3841, 2000; Todo et al., Mol. Ther. 2:588-595, 2000). Recently, G207 has been examined in patients with recurrent malignant glioma (Markert et al., Gene Ther. 7:867-874, 2000), and the results from this phase I clinical trial indicate that intracerebral inoculation of G207 is safe at doses of up to 3×10$^9$ plaque forming units (pfu), the highest dose tested. While the use of oncolytic viruses is a promising approach for cancer therapy, the therapeutic benefits will likely depend on the dose and route of administration, the extent of intratumoral viral replication, and the host immune response.

HSV-1 infection causes down-regulation of major histocompatibility complex (MHC) class I expression on the surface of infected host cells (Jennings et al., J. Virol. 56:757-766, 1985; Hill et al., J. Immunol. 152:2736-2741, 1994). The binding of ICP47 to the transporter associated with antigen presentation (TAP) blocks antigenic peptide transport in the endoplasmic reticulum and loading of MHC class I molecules (York et al., Cell 77:525-535, 1994; Hill et al., Nature 375:411-415, 1995; Früh et al., Nature 375:415-418, 1995). The binding of ICP47 is species-specific for TAPs from large mammals (Jugovic et al., J. Virol. 72:5076-5084, 1998), with the affinity for murine TAP about 100-fold less than for human (Ahn et al., EMBO J. 15:3247-3255, 1996).

SUMMARY OF THE INVENTION

The invention provides herpes simplex viruses (e.g., HSV-1 viruses) that include mutations within the BstEII-EcoNI fragment of the BamHIxfragment of the viruses. These viruses can also include, for example, an inactivating mutation in the γ34.5 neurovirulence locus of the viruses, and/or an inactivating mutation in the ICP6 locus of the viruses.

Also included in the invention are herpes simplex viruses (e.g., an HSV-1 virus) that include an inactivating mutation in the ICP47 locus of the viruses, in the absence of an inactivating mutation in the γ34.5 neurovirulence locuses of the virus. Optionally, these viruses also can include an inactivating mutation in the ICP6 locus of the viruses.

The invention also provides methods of inducing a systemic immune response to cancer in a patient, which involve administering to the patient a herpes virus that includes an inactivating mutation in the ICP47 locus of the herpes virus. The herpes virus can be administered, for example, to a tumor of the patient. In addition, the patient can have or be at risk of developing metastatic cancer, and the treatment can be carried out to treat or prevent such cancer. The inactivating mutation in the ICP47 locus of the herpes virus can be, for example, in the BstEII-EcoNI fragment of the BamHIxfragment of the virus. Optionally, the virus can include an inactivating mutation in the γ34.5 neurovirulence locus of the herpes virus, and/or an inactivating mutation in the ICP6 locus of the herpes virus.

The invention also provides herpes viruses that include a first mutation that inactivates the γ34.5 neurovirulence locus of the viruses and a second mutation that results in early expression of US11, in the absence of an ICP47-inactivating mutation in the BamHIxfragment of the viruses. Early expression of US11 can be achieved, for example, by inserting a promoter upstream from the US11 gene, or by inserting a US11 gene under the control of an early-expressing promoter into the genome of the virus. The viruses can also include a mutation that results in downregulation of ICP47 expression, in the absence of a mutation in the BamHIxfragment of the virus. The downregulation of ICP47 can be due to, for example, a deletion in, or inactivation of, the ICP47 promoter, or the fusion of ICP47 with a peptide that prevents functional expression of ICP47.

The invention also includes a herpes virus that includes a first mutation that inactivates the γ34.5 neurovirulence locus of the virus and a second mutation that results in downregulation of ICP47 expression, in the absence of a mutation in the BamHIxfragment of the virus. The downregulation of ICP47 can be due to, for example, a deletion in, or inactivation of, the ICP47 promoter, or the fusion of ICP47 with a peptide that prevents functional expression of ICP47.

The viruses described above can also include an additional mutation (e.g., a mutation in the ICP6 locus) to prevent reversion to wild type. The viruses can also include, optionally, sequences encoding a heterologous gene product, such as a vaccine antigen or an immunomodulatory protein. The viruses described herein can be herpes simplex viruses (HSV), such as herpes simplex-1 viruses (HSV-1).

The invention further provides pharmaceutical compositions that include any of the viruses described herein and a pharmaceutically acceptable carrier, adjuvant, or diluent, as well as methods of treating cancer in a patient, involving administering such a pharmaceutical composition to the patient. Also included in the invention are methods of immunizing a patient against an infectious disease, cancer, or an autoimmune disease, involving administering such a pharmaceutical composition to the patient.

The invention provides several advantages. For example, the viruses of the invention replicate in, and thus destroy, dividing cells, such as cancer cells, while not affecting other cells in the body. An additional advantage of the viruses of the invention in which ICP47 is deleted is that the immune response induced by such viruses is enhanced, which results in a better antitumor immune response. The viruses of the invention also include multiple mutations, eliminating the possibility of reversion to wild type. Moreover, although the viruses of the invention may have enhanced replication, this is not accompanied by increased toxicity. In addition, replication of herpes simplex viruses can be controlled through the action of antiviral drugs, such acyclovir, which block viral replication. These features render the viruses of the invention to be not only effective, but safe as well.

Other features and advantages of the invention will be apparent from the following detailed description, drawings, and claims.

BRIEF DESCRIPTION OF THE DRAWINGS

FIG. 1A is a schematic representation of the HSV-1 genome. FIG. 1B is an expanded map of the ICP47 locus, showing the locations of the overlapping 3' coterminal transcripts for US10, US11, and US12 (ICP47). FIG. 1C is a schematic representation of plasmid pIE12, which contains an 1818 basepair BamHI-EcoRI fragment from the HSV-1 BamHIxfragment, which encompasses the ICP47 region (Johnson et al., J. Virology 68(10):6347-6362, 1994). This plasmid can be used to introduce modifications into the ICP47 locus of the viral genome, as is described further below. FIG. 1D is a schematic representation of plasmid pIE12 Δ, which was derived from pIE12 by deleting 312 basepairs between the indicated BstEII and NruI sites. This plasmid was used to generate the γ34.5 suppressor mutants R47Δ and G47Δ. FIG. 1E is a schematic representation of the details of the 3' terminus of the ICP47 coding region. Sequences can be inserted into the indicated BstEII site, without disrupting sequences between the BstEII and NruI sites, for the purposes of changing the temporal regulation of the late US11 gene, to generate a γ34.5 suppressor function, and/or preventing functional expression of the ICP47 gene product.

FIG. 2A is a schematic of the HSV-1 genome showing the regions modified in G47Δ. The HSV-1 genome consists of long and short unique regions ($U_L$ and $U_S$), each bounded by terminal (T) and internal (I) repeat regions ($R_L$ and $R_S$). The parental virus G207 was engineered from wild-type HSV-1 strain F by deleting 1 kilobase within both copies of the γ34.5 gene, and inserting the E. coli lacZ gene into the ICP6 coding region. G47Δ was derived from G207 by deleting 312 basepairs from the ICP47 locus, as indicated. FIG. 2B is a map of the ICP47 locus, showing locations of the overlapping 3' co-terminal transcripts (US10, US11, and ICP47), open reading frames (thick arrow), and ICP47 splice junctions (^). FIG. 2C is a map of plasmid pIE12Δ, which was used to generate deletions by homologous recombination with the indicated flanking sequences. While US11 is regulated as a true late gene in wild-type HSV-1, deletion between the indicated BstEII and EcoNI sites places US11 under control of the ICP47 immediate-early promoter. Restriction site abbreviations are: B, BamHI; Bs, BstEII; E, EcoRI; EN, EcoNI; Nr, NruI.

FIG. 5A is a graph of flow cytometric analyses of MHC class I expression in Detroit 551 human fibroblast cells 48 hours after infection with HSV-1 (MOI=3). While all HSVs with an intact α47 gene (wild-type strain F and G207) significantly down-regulated MHC class I expression, G47Δ completely precluded the down-regulation. FIG. 5B is a graph showing a time course of MHC class I down-regulation in Detroit 551 cells infected with HSV-1. For each virus, the peak value of MHC class I expression at 6, 24, or 48 hours post-infection, analyzed by flow cytometry, was expressed as a percentage of the peak value of mock-infected cells (control) at each time point. MHC class I down-regulation by G207 and R3616 occurred in a time-dependent fashion. Dissociation of MHC class I expression between α47-deleted mutants (G47Δ and R47Δ) and α47-intact viruses became apparent at 24-48 hours post-infection. FIG. 5C is a series of graphs showing flow cytometric analyses of MHC class I expression in human melanoma cell lines 24 hours after infection with G207 and G47Δ. G47Δ caused a partial preclusion of MHC class I down-regulation in melanomas 1102 and 938, resulting in greater MHC class I expression than G207.

DETAILED DESCRIPTION

The invention provides viruses that can be used in therapeutic methods, such as, for example, in the treatment of cancer. These viruses are particularly well suited for this purpose, as they replicate in, and thus destroy, dividing cells (e.g., cancer cells), but they do not replicate substantially, and thus are avirulent, in non-dividing cells. The viruses of the invention can also be used in immunization methods, for the treatment or prevention of, for example, infectious diseases, cancer, or autoimmune diseases. An advantageous feature of many of the viruses of the invention is that, in addition to directly causing lysis of tumor cells, they induce a systemic immune response against tumors. Thus, these viruses can be used not only to treat a given tumor, to which they may be directly administered, but also to prevent or treat cancer metastasis.

Several of the viruses of the invention are herpes simplex viruses (HSV) that include an inactivating mutation in the ICP47 locus of the virus. This mutation can occur, for example, between the BstEII site and the EcoNI site of the BamHIxfragment of HSV-1, and may comprise, e.g., deletion of the BstEII-ExoNI fragment. Optionally, a herpes simplex virus including a mutation between the BstEII and EcoNI sites can also include additional mutations. For example, such a virus can include an inactivating mutation in the γ34.5 neurovirulence determination locus of the virus, and/or an inactivating mutation elsewhere in the genome, e.g., in the ICP6 locus. The invention also includes herpes simplex viruses that include inactivating mutations in the ICP47 locus, in the absence of an inactivating mutation in the γ34.5 neurovirulence locus. Optionally, such a virus can include an inactivating mutation in another, non-γ34.5 neurovirulence locus, e.g., in the ICP6 locus.

The invention includes additional viruses that are based on herpes viruses, such as herpes simplex (HSV viruses), for example, HSV-1 (e.g., HSV-1 strain F or strain Patton) or HSV-2, that include an inactivating mutation in a virulence gene. In the case of herpes simplex viruses, this mutation can be an inactivating mutation in the γ34.5 gene, which is the major HSV neurovirulence determinant. (See, e.g., FIG. 1 for details concerning the construction of examples of viruses that are included in the invention.)

Figures 1A, 1B, 1C, 1D, 1E:
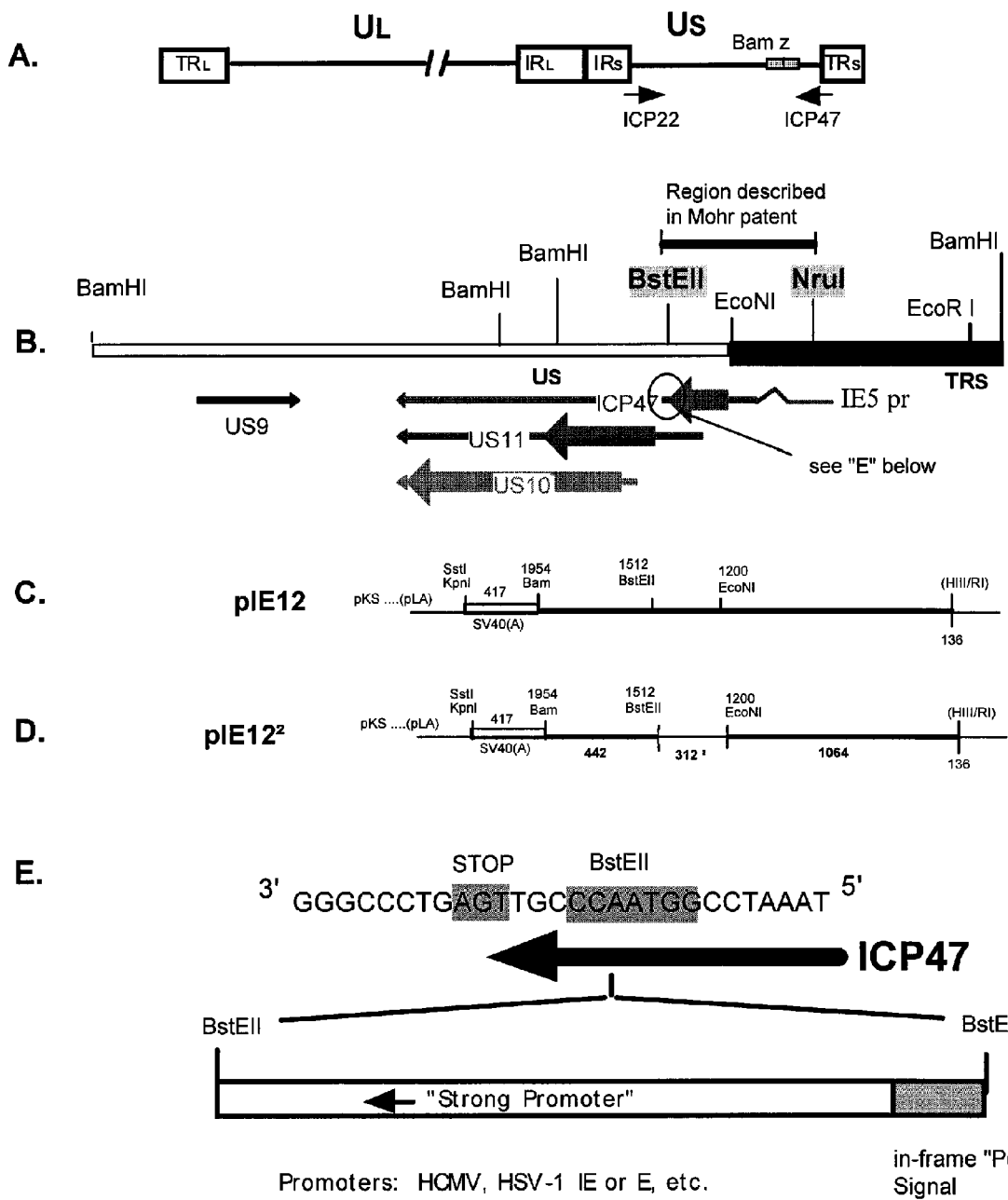
FIGS. 1A-1E are schematic representations of the HSV-1 genome and approaches to making vectors included in the invention.

In addition to the γ34.5 mutation, in one example, the viruses of the invention can include a modification that results in early expression of US11, in the absence of an ICP-47-inactivating mutation in the BamHIxfragment of the vector. US11 is normally expressed as a true-late gene, requiring DNA replication for its expression. However, early expression of US11 in some of the viruses of the invention can compensate for the γ34.5 defect by preventing the PKR-mediated shut-off of protein synthesis (see, e.g., FIG. 1E). Early expression of US11 in such a virus can be achieved by, for example, inserting an early-acting promoter upstream of the US11 gene (FIG. 1E). Such promoters can include, for example, the human cytomegalovirus (CMV) IE promoter, an HSV-1 IE promoter, an HSV-1 E promoter, or any other heterologous promoter that is active before the onset of DNA replication in the HSV-1 genome (see, e.g., below). An alternative approach to achieving early expression of US11 included in the invention involves inserting an exogenous copy of a US11 gene elsewhere in the viral genome, under the control of any suitable promoter that is active early in infection, such as one of those listed above, for example.

An additional HSV-based virus included in the invention includes, in addition to an inactivating mutation in the γ34.5 locus, a second modification that results in downregulation of ICP47 expression, in the absence of a mutation in the BamHIxfragment of the virus. In one example of such a virus, ICP47 coding sequences are fused with sequences that encode a peptide that prevents functional expression of ICP47 (see, e.g., FIG. 1E). Such a peptide can include, for example, a PEST sequence, which is rich in proline (P), glutamate (E), serine (S), and threonine (T), and thus provides intramolecular signals for rapid proteolytic degradation (Rechsteiner et al., Trends Biochem. Sci. 21(7):267-271, 1996). Such a poison sequence can be inserted into the virus at, for example, the BstEII site, upstream of a strong promoter driving US11 (FIG. 1E). In an alternative vector, signals that direct RNA degradation are incorporated into the virus, to direct degradation of ICP47 RNA.

Other viruses included in the invention can include, in addition to an inactivating mutation in the γ34.5 locus, two additional modifications. The first additional modification results in early expression of US11 and the second modification results in downregulation of ICP47 expression, as described above, in the absence of a mutation in the BamHIx fragment of the virus. In one example of such a virus, an early-expressing promoter is inserted upstream of the US11 gene and ICP47 coding sequences are fused with sequences encoding a poison sequence, such as a PEST sequence (FIG. 1E).

Any of the viruses described above and herein and elsewhere can include an additional mutation or modification that is made to prevent reversion of the virus to wild type. For example, the virus can include a mutation in the ICP6 gene (see below), which encodes the large subunit of ribonucleotide reductase. A specific example of a virus that is included in the invention, G47Δ, is described in further detail below. Briefly, this virus includes a deletion in the γ34.5 gene, an inactivating insertion in the ICP6 gene, and a 312 basepair deletion in the ICP47 gene.

The viruses described herein can be generated from any herpes virus family member, such as a neurotrophic, B-lymphotrophic, or T-lymphotrophic herpes virus. For example, a herpes simplex virus (HSV), such as HSV-1 or HSV-2, can be used. Alternatively, any of the following viruses can be used: Varicella-zoster virus (VZV), herpes virus 6 (HSV-6), Epstein Barr virus, cytomegalovirus, HHV6, and HHV7. The methods and viruses described herein are described primarily in reference to HSV-1, but these methods can readily be applied to any of these other viruses by one of skill in this art.

As is noted above, the viruses of the invention can be used to treat cancer, as these viruses replicate in, and thus destroy dividing cells, such as cancer cells, but are avirulent to other cells. Examples of cancer cells that can be destroyed, according to the invention, include cancer cells of nervous-system type tumors, for example, astrocytoma, oligodendroglioma, meningioma, neurofibroma, glioblastoma, ependymoma, Schwannoma, neurofibrosarcoma, neuroblastoma, pituitary tumor (e.g., pituitary adenoma), and medulloblastoma cells. Other types of tumor cells that can be killed, pursuant to the present invention, include, for example, melanoma, prostate carcinoma, renal cell carcinoma, pancreatic cancer, breast cancer, lung cancer, colon cancer, gastric cancer, fibrosarcoma, squamous cell carcinoma, neurectodermal, thyroid tumor, lymphoma, hepatoma, mesothelioma, and epidermoid carcinoma cells, as well as other cancer cells mentioned herein. Also as is noted above, the viruses of the invention, which induce a systemic immune response to cancer, can be used to prevent or to treat cancer metastasis.

Other therapeutic applications in which killing of a target cell is desirable include, for example, ablation of keratinocytes and epithelial cells responsible for warts, ablation of cells in hyperactive organs (e.g., thyroid), ablation of fat cells in obese patients, ablation of benign tumors (e.g., benign tumors of the thyroid or benign prostatic hypertrophy), ablation of growth hormone-producing adenohypophyseal cells to treat acromegaly, ablation of mammotropes to stop the production of prolactin, ablation of ACTH-producing cells to treat Cushing's disease, ablation of epinephrine-producing chromaffin cells of the adrenal medulla to treat pheochromocytoma, and ablation of insulin-producing beta islet cells to treat insulinoma. The viruses of the invention can be used in these applications as well.

The effects of the viruses of the invention can be augmented if the viruses also contain a heterologous nucleic acid sequence encoding one or more therapeutic products, for example, a cytotoxin, an immunomodulatory protein (i.e., a protein that either enhances or suppresses a host immune response to an antigen), a tumor antigen, an antisense RNA molecule, or a ribozyme. Examples of immunomodulatory proteins include, e.g., cytokines (e.g., interleukins, for example, any of interleukins 1-15, $\alpha$, $\beta$, or $\gamma$-interferons, tumor necrosis factor, granulocyte macrophage colony stimulating factor (GM-CSF), macrophage colony stimulating factor (M-CSF), and granulocyte colony stimulating factor (G-CSF)), chemokines (e.g., neutrophil activating protein (NAP), macrophage chemoattractant and activating factor (MCAF), RANTES, and macrophage inflammatory peptides MIP-1a and MIP-1b), complement components and their receptors, immune system accessory molecules (e.g., B7.1 and B7.2), adhesion molecules (e.g., ICAM-1, 2, and 3), and adhesion receptor molecules. Examples of tumor antigens that can be produced using the present methods include, e.g., the E6 and E7 antigens of human papillomavirus, EBV-derived proteins (Van der Bruggen et al., Science 254:1643-1647, 1991), mucins (Livingston et al., Curr. Opin. Immun. 4(5):624-629, 1992), such as MUC1 (Burchell et al., Int. J. Cancer 44:691-696, 1989), melanoma tyrosinase, and MZ2-E (Van der Bruggen et al., supra). (Also see WO 94/16716 for a further description of modification of viruses to include genes encoding tumor antigens or cytokines.)

As is noted above, the therapeutic product can also be an RNA molecule, such as an antisense RNA molecule that, by hybridization interactions, can be used to block expression of a cellular or pathogen mRNA. Alternatively, the RNA molecule can be a ribozyme (e.g., a hammerhead or a hairpin-based ribozyme) designed either to repair a defective cellular RNA, or to destroy an undesired cellular or pathogen-encoded RNA (see, e.g., Sullenger, Chem. Biol. 2(5): 249-253, 1995; Czubayko et al., Gene Ther. 4(9):943-949, 1997; Rossi, Ciba Found. Symp. 209:195-204, 1997; James et al., Blood 91(2):371-382, 1998; Sullenger, Cytokines Mol. Ther. 2(3):201-205, 1996; Hampel, Prog. Nucleic Acid Res. Mol. Bio. 58:1-39, 1998; Curcio et al., Pharmacol. Ther. 74(3):317-332, 1997).

A heterologous nucleic acid sequence can be inserted into a virus of the invention in a location that renders it under the control of a regulatory sequence of the virus. Alternatively, the heterologous nucleic acid sequence can be inserted as part of an expression cassette that includes regulatory elements, such as promoters or enhancers. Appropriate regulatory elements can be selected by those of ordinary skill in the art based on, for example, the desired tissue-specificity and level of expression. For example, a cell-type specific or tumor-specific promoter can be used to limit expression of a gene product to a specific cell type. This is particularly useful, for example, when a cytotoxic, immunomodulatory, or tumor antigenic gene product is being produced in a tumor cell in order to facilitate its destruction. In addition to using tissue-specific promoters, local administration of the viruses of the invention can result in localized expression and effect.

Examples of non-tissue specific promoters that can be used in the invention include the early Cytomegalovirus (CMV) promoter (U.S. Pat. No. 4,168,062) and the Rous Sarcoma Virus promoter (Norton et al., Molec. Cell. Biol. 5:281, 1985). Also, HSV promoters, such as HSV-1 IE and IE 4/5 promoters, can be used.

Examples of tissue-specific promoters that can be used in the invention include, for example, the prostate-specific antigen (PSA) promoter, which is specific for cells of the prostate; the desmin promoter, which is specific for muscle cells (Li et al., Gene 78:243, 1989; Li et al., J. Biol. Chem. 266:6562, 1991; Li et al., J. Biol. Chem. 268:10403, 1993); the enolase promoter, which is specific for neurons (Forss-Petter et al., J. Neuroscience Res. 16(1):141-156, 1986); the $\beta$-globin promoter, which is specific for erythroid cells (Townes et al., EMBO J. 4:1715, 1985); the tau-globin promoter, which is also specific for erythroid cells (Brinster et al., Nature 283:499, 1980); the growth hormone promoter, which is specific for pituitary cells (Behringer et al., Genes Dev. 2:453, 1988); the insulin promoter, which is specific for pancreatic $\beta$ cells (Selden et al., Nature 321:545, 1986); the glial fibrillary acidic protein promoter, which is specific for astrocytes (Brenner et al., J. Neurosci. 14:1030, 1994); the tyrosine hydroxylase promoter, which is specific for catecholaminergic neurons (Kim et al., J. Biol. Chem. 268: 15689, 1993); the amyloid precursor protein promoter, which is specific for neurons (Salbaum et al., EMBO J. 7:2807, 1988); the dopamine $\beta$-hydroxylase promoter, which is specific for noradrenergic and adrenergic neurons (Hoyle et al., J. Neurosci. 14:2455, 1994); the tryptophan hydroxylase promoter, which is specific for serotonin/pineal gland cells (Boularand et al., J. Biol. Chem. 270:3757, 1995); the choline acetyltransferase promoter, which is specific for cholinergic neurons (Hersh et al., J. Neurochem. 61:306, 1993); the aromatic L-amino acid decarboxylase (AADC) promoter, which is specific for catecholaminergic/ 5-HT/D-type cells (That et al., Mol. Brain. Res. 17:227, 1993); the proenkephalin promoter, which is specific for neuronal/spermatogenic epididymal cells (Borsook et al., Mol. Endocrinol. 6:1502, 1992); the reg (pancreatic stone protein) promoter, which is specific for colon and rectal tumors, and pancreas and kidney cells (Watanabe et al., J. Biol. Chem. 265:7432, 1990); and the parathyroid hormone-related peptide (PTHrP) promoter, which is specific for liver and cecum tumors, and neurilemoma, kidney, pancreas, and adrenal cells (Campos et al., Mol. Rnfovtinol. 6:1642, 1992).

Examples of promoters that function specifically in tumor cells include the stromelysin 3 promoter, which is specific for breast cancer cells (Basset et al., Nature 348:699, 1990); the surfactant protein A promoter, which is specific for non-small cell lung cancer cells (Smith et al., Hum. Gene Ther. 5:29-35, 1994); the secretory leukoprotease inhibitor (SLPI) promoter, which is specific for SLPI-expressing carcinomas (Garver et al., Gene Ther. 1:46-50, 1994); the tyrosinase promoter, which is specific for melanoma cells (Vile et al., Gene Therapy 1:307, 1994; WO 94/16557; WO 93/GB1730); the stress inducible grp78/BiP promoter, which is specific for fibrosarcoma/tumorigenic cells (Gazit et al., Cancer Res. 55(8):1660, 1995); the AP2 adipose enhancer, which is specific for adipocytes (Graves, J. Cell. Biochem. 49:219, 1992); the $\alpha$-1 antitrypsin transthyretin promoter, which is specific for hepatocytes (Grayson et al., Science 239:786, 1988); the interleukin-10 promoter, which is specific for glioblastoma multiform cells (Nitta et al., Brain Res. 649:122, 1994); the c-erbB-2 promoter, which is specific for pancreatic, breast, gastric, ovarian, and non-small cell lung cells (Harris et al., Gene Ther. 1:170, 1994); the $\alpha$-B-crystallin/heat shock protein 27 promoter, which is specific for brain tumor cells (Aoyama et al., Int. J. Cancer 55:760, 1993); the basic fibroblast growth factor promoter, which is specific for glioma and meningioma cells (Shibata et al., Growth Fact. 4:277, 1991); the epidermal growth factor receptor promoter, which is specific for squamous cell carcinoma, glioma, and breast tumor cells (Ishii et al., Proc. Natl. Acad. Sci. U.S.A. 90:282, 1993); the mucin-like glycoprotein (DF3, MUC1) promoter, which is specific for breast carcinoma cells (Abe et al., Proc. Natl. Acad. Sci. U.S.A. 90:282, 1993); the mts1 promoter, which is specific for metastatic tumors (Tulchinsky et al., Proc. Natl. Acad. Sci. U.S.A. 89:9146, 1992); the NSE promoter, which is specific for small-cell lung cancer cells (Forss-Petter et al., Neuron 5:187, 1990); the somatostatin receptor promoter, which is specific for small cell lung cancer cells (Bombardieri et al., Eur. J. Cancer 31A:184, 1995; Koh et al., Int. J. Cancer 60:843, 1995); the c-erbB-3 and c-erbB-2 promoters, which are specific for breast cancer cells (Quin et al., Histopathology 25:247, 1994); the c-erbB4 promoter, which is specific for breast and gastric cancer cells (Rajkumar et al., Breast Cancer Res. Trends 29:3, 1994); the thyroglobulin promoter, which is specific for thyroid carcinoma cells (Mariotti et al., J. Clin. Endocrinol. Meth. 80:468, 1995); the $\alpha$-fetoprotein promoter, which is specific for hepatoma cells (Zuibel et al., J. Cell. Phys. 162:36, 1995); the villin promoter, which is specific for gastric cancer cells (Osborn et al., Virchows Arch. A. Pathol. Anat. Histopathol. 413:303, 1988); and the albumin promoter, which is specific for hepatoma cells (Huber, Proc. Natl. Acad. Sci. U.S.A. 88:8099, 1991).

As is noted above, the viruses of the invention can be used in in vivo methods, for example, to kill a cell and/or to introduce a therapeutic gene product into the cell. To carry out these methods, the viruses of the invention can be administered by any conventional route used in medicine. For example, a virus of the invention can be administered directly into a tissue in which an effect, e.g., cell killing and/or therapeutic gene expression, is desired, for example, by direct injection or by surgical methods (e.g., stereotactic injection into a brain tumor; Pellegrino et al., Methods in Psychobiology (Academic Press, New York, N.Y., 67-90, 1971)). An additional method that can be used to administer vectors into the brain is the convection method described by Bobo et al. (Proc. Natl. Acad. Sci. U.S.A. 91:2076-2080, 1994) and Morrison et al. (Am. J. Physiol. 266:292-305, 1994). In the case of tumor treatment, as an alternative to direct tumor injection, surgery can be carried out to remove the tumor, and the vectors of the invention inoculated into the resected tumor bed to ensure destruction of any remaining tumor cells. Alternatively, the vectors can be administered via a parenteral route, e.g., by an intravenous, intraarterial, intracerebroventricular, subcutaneous, intraperitoneal, intradermal, intraepidermal, or intramuscular route, or via a mucosal surface, e.g., an ocular, intranasal, pulmonary, oral, intestinal, rectal, vaginal, or urinary tract surface.

Any of a number of well-known formulations for introducing viruses into cells in mammals, such as humans, can be used in the invention. (See, e.g., Remington's Pharmaceutical Sciences (18$^{th}$ edition), ed. A. Gennaro, 1990, Mack Publishing Co., Easton, Pa.) However, the viruses can be simply diluted in a physiologically acceptable solution, such as sterile saline or sterile buffered saline, with or without an adjuvant or carrier.

The amount of virus to be administered depends, e.g., on the specific goal to be achieved, the strength of any promoter used in the virus, the condition of the mammal (e.g., human) intended for administration (e.g., the weight, age, and general health of the mammal), the mode of administration, and the type of formulation. In general, a therapeutically or prophylactically effective dose of, e.g., from about $10^1$ to $10^{10}$ plaque forming units (pfu), for example, from about $5 \times 10^4$ to $1 \times 10^6$ pfu, e.g., from about $1 \times 10^5$ to about $4 \times 10^5$ pfu, although the most effective ranges may vary from host to host, as can readily be determined by one of skill in this art. Also, the administration can be achieved in a single dose or repeated at intervals, as determined to be appropriate by those of skill in this art.

A specific example of a virus of the invention, designated G47Δ, which is a new, multimutated, replication-competent HSV-1 virus, derived from G207 by a deletion within the non-essential α47 gene (Mavromara-Nazos et al., J. Virol. 60:807-812, 1986), is now described. Because of the overlapping transcripts encoding ICP47 and US11 (FIG. 2B), the deletion in α47 also places the late US11 gene under control of the immediate-early α47 promoter. This enhances the growth properties of γ34.5$^-$ mutants by precluding the shut-off of protein synthesis (Mohr et al., EMBO J. 15:4759-4766, 1996; He et al., J. Virol. 71:6049-6054, 1997; Cassady et al., J. Virol. 72:7005-7011, 1998; Cassady et al., J. Virol. 72:8620-8626, 1998). Nevertheless, we found that G47Δ was as safe as G207, which is now in clinical trials in humans, when inoculated into the brains of A/J mice at $2 \times 10^6$ pfu. We show here that human melanoma cells infected with G47Δ were more effective at stimulating their matched tumor-infiltrating lymphocytes (TILs) than those infected with G207, that G47Δ showed enhanced replication in cultured tumor cells, and that G47Δ was more efficacious than G207 at inhibiting tumor growth in both human xenograft and mouse syngeneic tumor models tested. Our results show that G47Δ can be used for tumor therapy. Additional details of this virus and its properties are provided as follows.

EXPERIMENTAL RESULTS

Construction and Replication of G47Δ

G47Δ was constructed by deleting 312 basepairs from G207 in the $U_S$ region adjacent to $TR_S$ (FIG. 2). Southern blot analyses of G47Δ DNA confirmed the presence of a 0.3 kilobase deletion in the α47 gene and a 1 kilobase deletion in the γ34.5 gene. R47Δ, with the same deletion in the α47 locus, was generated from R3616, the parental virus of G207 that has an active ribonucleotide reductase (Chou et al., Science 250:1262-1266, 1990).

Figure 3:
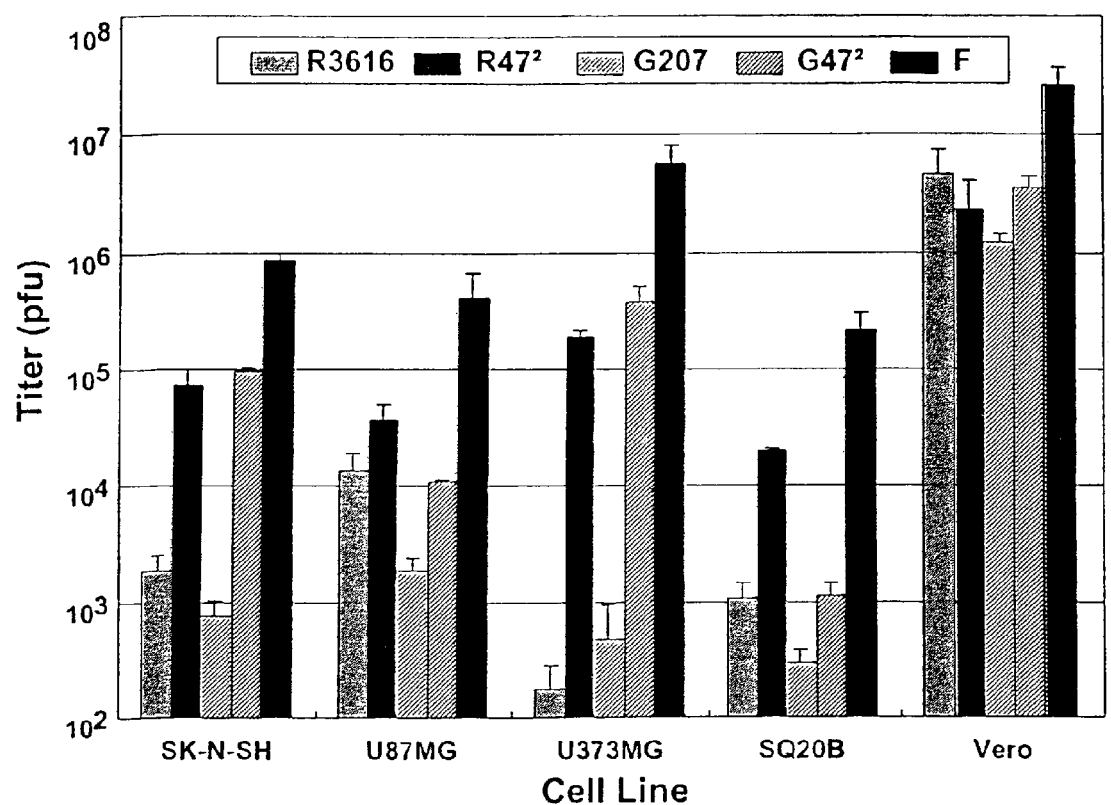
FIG. 3 is a graph showing virus yields of replication-competent HSV-1 mutants in various cell lines. Cells were seeded on 6 well plates at $5 \times 10^5$ cells/well. Triplicate wells were infected with R3616, R47Δ, G207, G47Δ, or strain F at a MOI of 0.01. At 24 hours post-infection, cells were scraped into the medium and progeny virus was titered on Vero cells. In all cell lines tested, G47Δ showed a significantly higher replication capability than G207. Results represent the mean of triplicates±SD.

To investigate the effects of the α47 deletion on the growth properties of γ34.5-deficient mutants (G207 and R3616), we determined the yield of progeny virus following infection of human tumor cells lines SK-N-SH (neuroblastoma), U87MG (glioma), U373MG (glioma), and SQ20B (head and neck squamous cell carcinoma). By 24 hours post-infection at a low MOI, G47Δ produced higher yields than G207, resulting in an approximately 4 to 1000-fold increase in titer (FIG. 3). In a single-step growth experiment in U87MG cells (MOI=2), the virus yield of G47Δ was 12 times greater than with G207. R47Δ similarly yielded higher titers than its parent R3616 in all tumor cell lines tested; however, neither G47Δ nor R47Δ grew as well as wild-type parental strain F. To determine whether virus yields were affected by cell density, Vero and SK-H-SH cells were seeded at normal or high density ($8 \times 10^5$ or $1.6 \times 10^6$ cells/well), infected with strain F, G207, or G47Δ at a MOI of 0.01, and harvested 48 hours post-infection. G47Δ produced a higher yield in the high-density culture, as opposed to G207, which had a reduced yield. The ability to generate higher yields of G47Δ in Vero cells facilitates manufacturing of high titer stocks for clinical use.

Cytopathic Effect of G47Δ In Vitro

Figure 4:
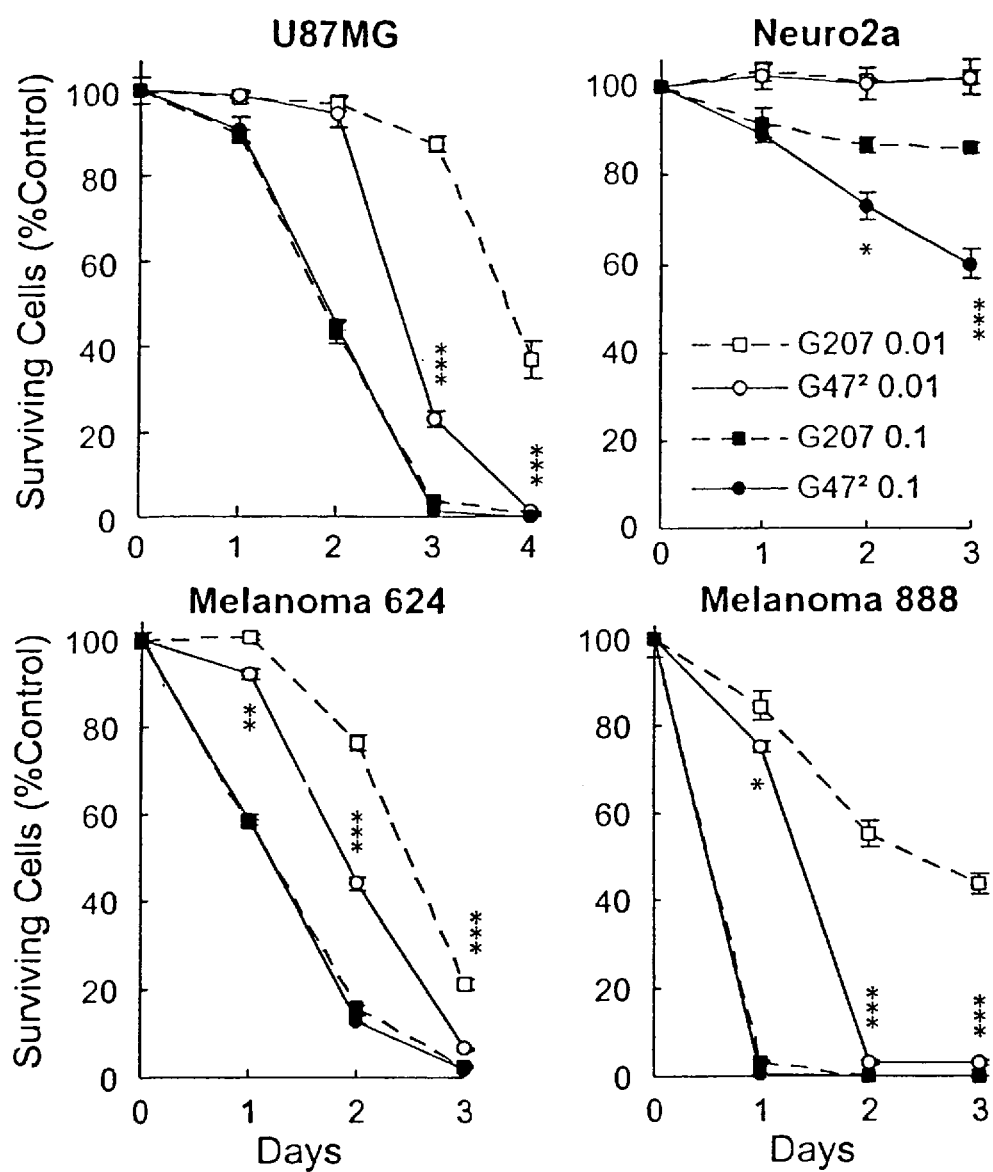
FIG. 4 is a series of graphs showing the cytopathic effect of G47Δ in vitro. Cells were plated into 6 well plates at $2 \times 10^5$ cells/well. After 24 hours of incubation, cells were infected with G207 or G47Δ at a MOI of 0.01 or 0.1, or without virus (Control). The number of surviving cells was counted daily and expressed as a percentage of mock-infected controls. G47Δ exhibited a significantly stronger cytopathic effect than G207 in all three human tumor cell lines (U87MG and melanomas 624 and 888) at a MOI of 0.01, and also in Neuro2a murine neuroblastoma cells at a MOI of 0.1. The results are the mean of triplicates±SD. * $p<0.05$,  $p<0.01$, * $p<0.001$, G207 versus G47Δ, unpaired t test.

The cytolytic activity of G47Δ in vitro was compared to that of G207 in various neural crest-derived tumor cell lines. In human cell lines, U87MG and melanomas 624 and 888, G47Δ killed tumor cells significantly more rapidly than G207 at a low MOI of 0.01 (FIG. 4). At a MOI of 0.1, both G207 and G47Δ killed all the cells within 1-3 days of infection. Neuro2a, a murine neuroblastoma cell line, was resistant to killing by both G207 and G47Δ at a MOI of 0.01. At a MOI of 0.1, G47Δ was significantly more efficient at destroying tumor cells than G207 (FIG. 4), an effect also seen with N18 mouse neuroblastoma cells. We have found that mouse tumor cells are generally more resistant to G207 replication than human tumor cells (Todo et al., Hum. Gene Ther. 10:2741-2755, 1999; Toda et al., Hum. Gene Ther. 10:385-393, 1999; Todo et al., Cancer Res. 61:153-161, 2001).

MHC Class I Expression in G47Δ-Infected Cells

Figures 5A, 5B, 5C:
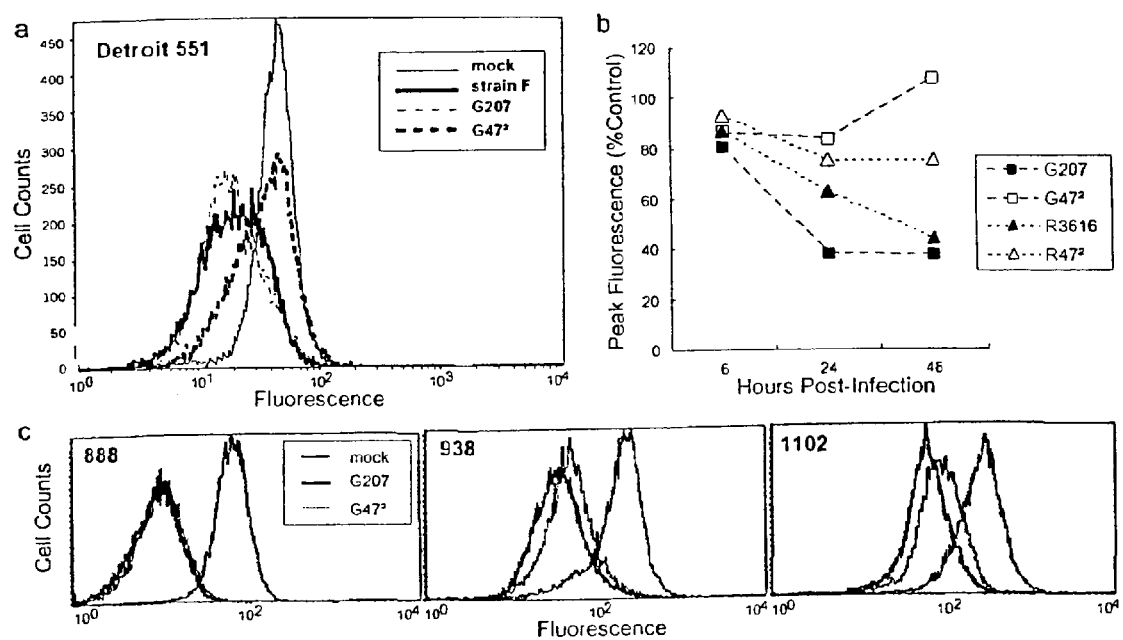
FIGS. 5A-5C are a series of graphs showing that G4F7Δ precludes down-regulation of MHC class I expression in infected host cells.

ICP47 inhibits the function of TAP in translocating peptides across the endoplasmic reticulum in human cells, but not in mouse or rat cells (Ahn et al., EMBO J. 15:3247-3255, 1996; Tomazin et al., J. Virol. 72:2560-2563, 1998). Because G47Δ lacks ICP47, infected cells should have levels of MHC class I expression typical of uninfected cells. We examined MHC class I down-regulation in Detroit 551 human diploid fibroblasts using flow cytometric analyses for human lymphocyte antigen class I (HLA-1). At 48 hours post-infection, all cells infected with HSV-1 containing an intact α47 gene (strain F, G207, and R3616) showed a decrease in cell surface MHC class I, resulting in approximately 40% in peak levels compared to mock-infected control cells (FIGS. 5A and 5B). By contrast, there was no down-regulation in G47Δ infected cells (FIG. 5A). In R47Δ-infected cells, MHC class I expression remained higher than in strain F or R3616-infected cells, but was reduced compared to G47Δ (~75% of mock-infected peak levels). Studies at different time points (6, 24, and 48 hours post-infection) revealed that differences in MHC class I down-regulation between ICP47 expressing (G207 and R3616) and non-expressing (G47Δ and R47Δ) infected cells did not become apparent until after 6 hours post-infection (FIG. 5B).

Infection of human melanoma cells with G47Δ also resulted in higher levels of MHC class I expression than with G207, although the preclusion of down-regulation was partial. In general, a greater effect was observed in cell lines with high basal levels of MHC class I (938 and 1102) compared to those with low levels of MHC class I (624, 888, and 1383) (FIG. 5C).

G47Δ-Infected Human Melanoma Cells Stimulate Human T Cells In Vitro

Figure 6:
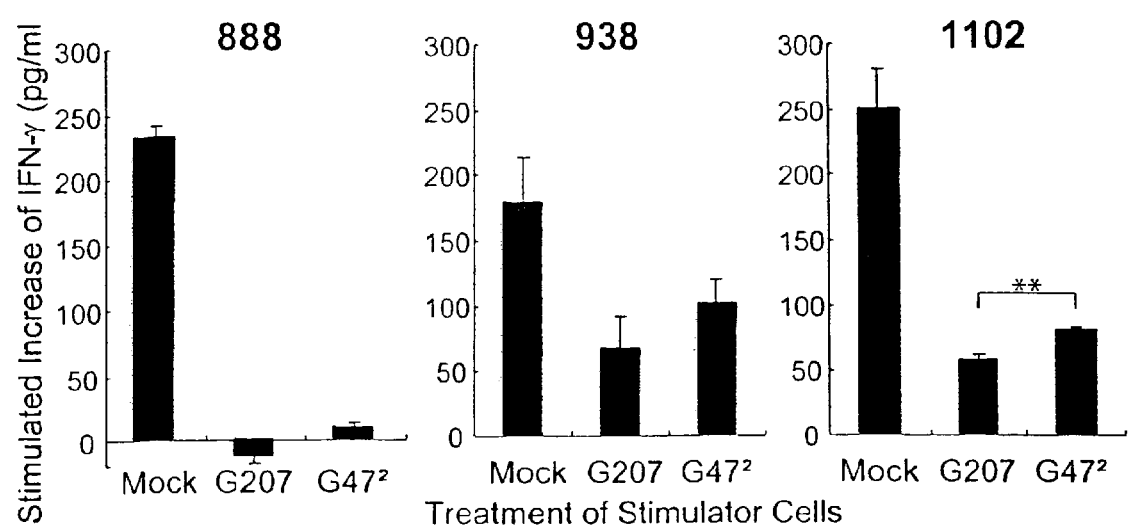
FIG. 6 is a series of graphs showing that G47Δ-infected tumor cells stimulate T cells to a greater extent than G207-infected tumor cells. Human melanoma cells were infected with mock (no virus), G207, or G47Δ at a MOI of 3, and after 3-6 hours, co-cultured with an equal number of responding human T cells for 18 hours. T cell stimulation was assessed by an increase in IFN-γ release into conditioned media. G47Δ-infected melanoma 1102 cells caused a significantly greater stimulation of TIL888 cells compared with G207-infected 1102 cells ($p<0.01$, unpaired t test). G47Δ-infected 938 melanoma cells also stimulated TIL1413 cells, although the improvement was not statistically significant compared with G207-infected 938 cells ($p=0.1$, unpaired t test). Neither G207 nor G47Δ-infected melanoma 888 cells caused a significant stimulation of TIL888 cells.

Three human melanoma cell lines were tested for their abilities to stimulate the matched TIL lines after G47Δ infection (888 and 1102 with TIL888 (Robbins et al., Cancer Res. 54:3124-3126, 1994)), and 938 with TIL1413 (Kang et al., J. Immunol. 155:1343-1348, 1995). G47Δ-infected 1102 melanoma cells, with the highest level of MHC class I expression, caused a better stimulation of TIL cells compared to G207-infected cells, resulting in 41% more IFN-γ secretion (FIG. 6). There was essentially no stimulation of this same TIL line with G47Δ or G207-infected 888 melanoma cells, which had very low levels of MHC class I expression. G47Δ-infected 938 melanoma cells stimulated TIL1413 cells, causing an increase in IFN-γ secretion that was not statistically significant. The results demonstrate that the higher MHC class I expression that may ensue in G47Δ versus G207-infected cells can enhance T cell stimulation.

Antitumor Efficacy of G47Δ In Vivo

Figure 7:
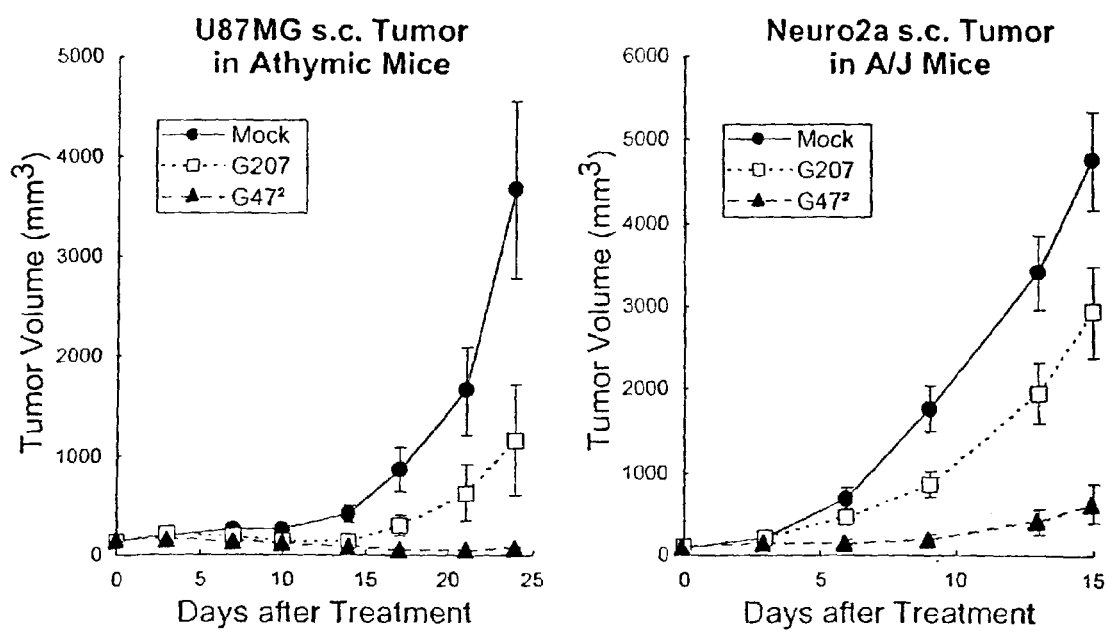
FIG. 7 is a set of graphs showing that G47Δ exhibits greater antitumor efficacy than G207 in vivo. Subcutaneous tumors of U87MG human glioma (Left) or Neuro2a murine neuroblastoma (Right) were generated in 6-week-old female athymic mice or 6-week-old female A/J mice, respectively. Established tumors of approximately 6 mm in diameter were inoculated with G207 or G47Δ ($1\times10^6$ pfu), or mock (PBS with 10% glycerol) on days 0 and 3. G47Δ treatment was significantly more efficacious than G207 in both tumor models, resulting in smaller average tumor volumes ($p<0.05$ for U87MG on day 24 and $p<0.001$ for Neuro2a on day 15, G207 versus G47Δ, unpaired t test).

In a human xenograft model, athymic mice harboring established subcutaneous U87MG glioma tumors (approximately 6 mm in diameter), intraneoplastic inoculation of G207 or G47Δ ($10^6$ pfu) followed by a second inoculation 3 days later caused a significant reduction in U87MG tumor growth ($p<0.05$ and $p<0.001$ versus control on day 24, respectively; unpaired t test; FIG. 7). G47Δ treatment was significantly more efficacious than G207, resulting in reduced average tumor volumes (FIG. 7). This was reflected in the prolonged survival of animals and number of 'cures' (complete tumor regression with no tumor regrowth during a 3-month follow up) (Table 1). At the dose tested, survival was significantly prolonged in the G207-treatment group ($p<0.05$ versus mock, Wilcoxon test), and to an even greater extent in the G47Δ-treated animals ($p<0.05$ versus G207, Wilcoxon test).

TABLE 1

Subcutaneous tumor therapy by G47Δ

|  | Number cured/total treated | | |
|---|---|---|---|
| Tumor (Mouse) | Mock | G207 | G47Δ |
| U87MG (Athymic) | 0/13 | 3/12 | 8/12*† |
| Neuro2a (A/J) | 0/10 | 1/10 | 3/10 |

*p < 0.05 versus G207,
†p < 0.001 versus Mock, Fisher's test.

The efficacy of G47Δ was further tested in an immunocompetent mouse tumor model, subcutaneous, poorly immunogenic Neuro2a neuroblastoma tumors in syngeneic A/J mice. Established tumors of approximately 6 mm in diameter were inoculated with mock, G207, or G47Δ ($10^6$ pfu) on days 0 and 3. Again, while both G207 and G47Δ caused a significant reduction in Neuro2a tumor growth ($p<0.05$ and $p<0.001$ versus control on day 15, respectively; unpaired t test), the efficacy of G47Δ was greater than that of G207 (FIG. 7). Kaplan-Meier analysis demonstrated that G207 at this dose did not significantly extend the survival of Neuro2a tumor-bearing A/J mice, whereas G47Δ significantly prolonged survival of the animals compared with mock and G207 ($p<0.01$ and $p<0.05$, respectively, Wilcoxon test). In a 3.5-month follow-up period, there was an increased number of 'cures' among the G47Δ-treated mice (not statistically significant, Fisher's test; Table 1).

Safety of G47Δ with Intracerebral Inoculation

To evaluate the toxicity of G47Δ in the brain, A/J mice were inoculated intracerebrally with mock, strain F ($2\times10^3$ pfu), G207 ($2\times10^6$ pfu), or G47Δ ($2\times10^6$ pfu). This dose was the highest dose obtainable for G207 in the volume injected. Each mouse was monitored daily for clinical manifestations for 3 weeks. All 8 mock-inoculated mice survived without any abnormal manifestations, whereas all 10 strain F-inoculated mice deteriorated rapidly and became moribund within 7 days of inoculation. All 8 G207-inoculated mice and 10 G47Δ-inoculated mice survived. Two of the G207-inoculated mice and 1 G47Δ-inoculated mouse temporarily manifested (3-6 days post-inoculation) slight hunching or a slightly sluggish response to external stimuli. This shows that G47Δ is as safe as G207 when inoculated in the brain of A/J mice at this dose.

The results described above were obtained using the following Materials and Methods.

Materials and Methods

Cells

Vero (African green monkey kidney), SK-N-SH (human neuroblastoma), U87MG (human glioma), U373MG (human glioma), Neuro2a (murine neuroblastoma), and Detroit 551 (diploid human fibroblast) cell lines were purchased from American Type Culture Collection (Rockville, Md.). SQ20B (head and neck squamous cell carcinoma) cells were provided by Dr. R. Weichselbaum (University of Chicago, Chicago, Ill.). N18 murine neuroblastoma cells were provided by Dr. K. Ikeda (Tokyo Institute of Psychiatry, Tokyo, Japan). Human melanoma cell lines 624, 888, 938, 1102, and 1383, and human T cell lines TIL888 and TIL1413, were provided by Dr. J. Wunderlich (NIH, Bethesda, Md.). All tumor cells were maintained in Dulbecco's modified Eagle medium supplemented with 10% fetal calf serum (FCS), 2 mM glutamine, penicillin (100 U/ml), streptomycin (100 µg/ml), and 2.5 µg/ml Fungizone. Human T cells were maintained in AIM-V medium (Gibco BRL, Life Technologies, Rockville, Md.) supplemented with 10% human serum (type AB, Rh+; Valley Biomedical Products, Winchester, Va.), interleukin 2 (600 international units (IU)/ml, Chiron Corporation, Emeryville, Calif.), penicillin (50 U/ml), and 1.25 µg/ml Fungizone.

Generation of G47Δ

Figures 2A, 2B, 2C:
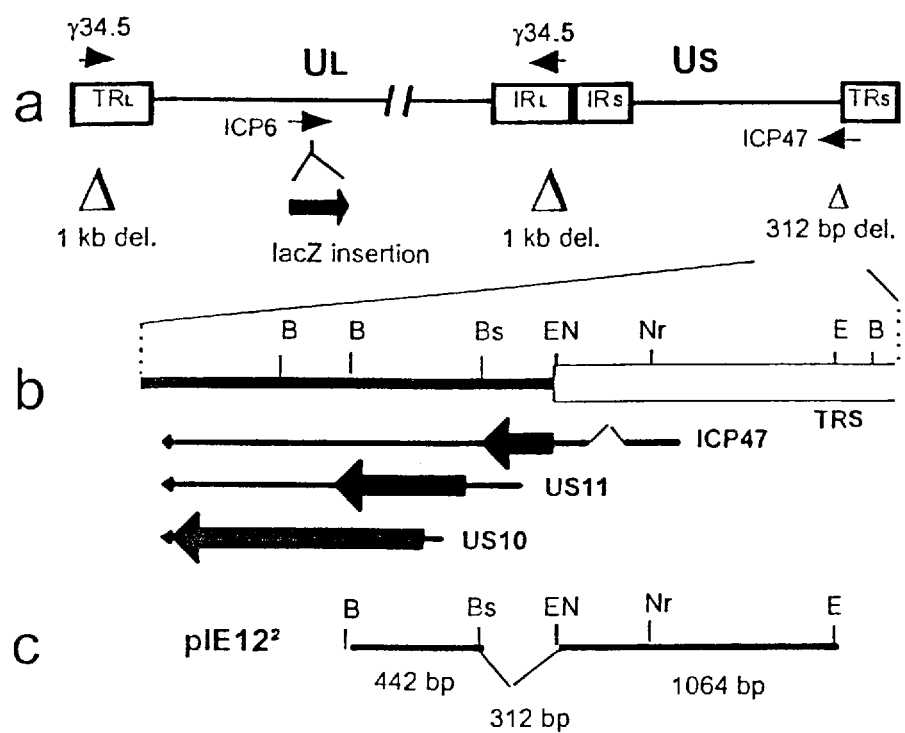
FIGS. 2A-2C are schematic representations of the structure of G47Δ.

Plasmid pIE12 contains an 1818 basepair BamHI-EcoRI fragment from the HSV-1 BamHIxfragment, which encompasses the ICP47 coding region (Johnson et al., J. Virol. 68:6347-6362, 1994). A 312 basepair fragment containing the ICP47 coding region between the BstEII and EcoNI sites was deleted from pIE12 to create pIE12 Δ (FIG. 2C). Vero cells were seeded on 6-well dishes at a density of $1-2\times10^5$ cells per well. Transfections were performed using a range of DNA concentrations from 1 to 3 µg, including a 1:1:1 mixture of G207 DNA (Mineta et al., Nat. Med. 1:938-943, 1995), pIE12 (intact), and pIE12 Δ cleaved with BamHI and XhoI, with 8 µl LipofectAMINE™ (Life Technologies), according to the manufacturer's instructions. The viral progeny from the transfection were then passaged twice in SK-N-SH cells to enrich for recombinants that contained a deletion in ICP47 as follows. SK-N-SH cells were seeded at a density of $5\times10^6$ cells per 10 cm dish, infected the following day at a range of MOI's from 0.01 to 1 pfu per cell, and harvested at 48 hours post-infection. This process was then repeated. The deletion in pIE12 Δ was designed to generate a second-site suppressor mutation of γ34.5 in the virus, and thus permit growth of successful recombinants on SK-N-SH cells (Mohr et al., EMBO J. 15:4759-4766, 1996). Individual plaques from SK-N-SH-enriched stocks were plaque-purified on Vero cells under agarose overlays and screened for the presence of the deletion in ICP47 by Southern blotting. A stock was prepared from one individual plaque that was homogeneous for the ICP47 deletion and designated as G47Δ. R47Δ was constructed similarly, except R3616 (Chou et al., Science 250:1262-1266, 1990) DNA was used in place of G207 DNA (R3616 was provided by Dr. B. Roizman, University of Chicago, Chicago, Ill.). Virus titration was performed as previously described (Miyatake et al., J. Virol. 71:5124-5132, 1997).

Virus Yield Studies

Cells were seeded on 6-well plates at $5\times10^5$, $8\times10^5$, or $1.6\times10^6$ cells per well. Triplicate or duplicate wells were infected with the viruses 6-8 hours after seeding at a MOI of 0.01. At 24 or 48 hours post-infection, the cells were scraped into the medium and lysed by three cycles of freeze-thawing. The progeny virus was titered as previously described with a modification (Miyatake et al., J. Virol. 71:5124-5132, 1997). Briefly, Vero cells were plated in 6-well plates at $8\times10^5$ cells/well. After 4-8 hours incubation at 37° C., cells were infected in 1 ml growth medium at 37° C. overnight, after which 1 ml medium containing 0.4% human IgG (ICN Pharmaceuticals) was added. Wells were incubated at 37° C. for another 2 days, and the number of plaques was counted after staining with methylene blue (0.5% w/v in 70% methanol).

In Vitro Cytotoxicity Studies

In vitro cytotoxicity studies were performed as previously described (Todo et al., Hum. Gene Ther. 10:2741-2755, 1999), with a modification for human melanoma cells, which were grown in medium containing 10% FCS. The number of surviving cells was counted daily with a Coulter counter (Beckman Coulter, Fullerton, Calif.) and expressed as a percentage of mock-infected controls.

Flow Cytometric Analyses

Cells were plated in 6 well plates at $1\times10^6$ cells/well and infected with virus (MOI=3) 24 hours after seeding. Cells were incubated in the presence of ganciclovir (200 ng/ml) at 39.5° C. for 6, 24, or 48 hours, harvested by trypsinization, and washed once with 2 ml PBS. G207 and G47Δ contain temperature-sensitive mutations in ICP4, so they can replicate at 37° C., but not at 39.5° C. (Mineta et al., Nat. Med. 1:938-943, 1995. Approximately 5×10⁵ cells were then used for flow cytometric analyses using FITC-conjugated anti-human HLA class I antigen (clone W6/32, Sigma, St. Louis, Mo.) and performed as previously described.

Human T Cell Stimulation Assays

Human melanoma cells (888, 938, or 1102) were plated in 6 well plates at 5×10⁵ cells/well, and infected with G207 or G47Δ (MOI=3), or without virus (mock) 24 hours after seeding. Cells were incubated in growth medium containing 10% FCS and ganciclovir (200 ng/ml) at 39.5° C. for 3 hours (888) or 6 hours (938 and 1102). Cells were then harvested by scraping, and a portion was used for cell counting. Infected melanoma cells (1×10⁵) were then co-cultured with an equal number of responding human T cells in 200 μl AIM-V medium containing ganciclovir (200 ng/ml) in a flat-bottom 96-well plate. Melanomas 888 and 1102 were co-cultured with TIL888 cells, and melanoma 938 was cultured with TIL1413 cells. TIL lines 888 and 1413 both recognize tyrosinase, a melanoma antigen, in an HLA-A24 restricted fashion (Robbins et al., Cancer Res. 54:3124-3126, 1994; Kang et al., J. Immunol. 155:1343-1348, 1995). After an 18 hour incubation at 37° C., the plate was centrifuged at 800 g for 10 minutes, and conditioned medium was collected. IFN-γ concentrations were measured by enzyme-linked immunosorbent assay using a human IFN-γ ELISA kit (Endogen, Woburn, Mass.). The IFN-γ measurements in TIL cells without stimulator cells were considered the base release levels and used to calculate the increase of IFN-γ secretion in stimulated TIL cells.

Animal Studies

Six-week-old female A/J mice and athymic nude mice (BALB/c nu/nu) were purchased from the National Cancer Institute (Frederick, Md.), and caged in groups of four or less. Subcutaneous tumor therapy was performed as previously described (Todo et al., Hum. Gene Ther. 10:2741-2755, 1999; Todo et al., Cancer Res. 61:153-161, 2001).

Intracerebral Inoculation Toxicity Studies

Mock (PBS containing 10% glycerol), strain F (2×10³ pfu), G207 (2×10⁶ pfu), or G47Δ (2×10⁶ pfu) in a volume of 5 μl was injected over 5 minutes into the right hemisphere of the brains of 6-week-old female A/J mice (n=8, 10, 8, and 10, respectively) using a KOPF stereotactic frame. Cages were then blinded and mice monitored daily for clinical manifestations for 3 weeks.

All references cited herein are incorporated by reference in their entirety. Other embodiments are within the following claims.

What is claimed is:

1. A method of treating cancer of the nervous system in a patient, said method comprising administering to a patient having cancer of the nervous system a herpes simplex virus-1, wherein said herpes simplex virus-1 comprises:
    an inactivating mutation in the ICP47 locus of said virus, wherein said mutation occurs between the BstEII site and the EcoNI site of the BamHI fragment encompassing the ICP47 region, and said mutation places US11 under control of the ICP47 immediate-early promoter that results in early expression of US11;
    an inactivating mutation in the γ34.5 neurovirulence locus of said virus; and
    an inactivating mutation in the ICP6 locus of said virus.

2. The method of claim 1, wherein the patient has or is at risk of developing one or more metastases.

3. The method of claim 1, wherein said herpes simplex virus-1 is administered to a tumor of said patient.

4. The method of claim 1, wherein said herpes simplex virus-1 is administered parenterally to said patient.

5. The method of claim 1, wherein said herpes simplex virus-1 further comprises sequences encoding a heterologous gene product.

6. The method of claim 5, wherein said heterologous gene product comprises a vaccine antigen or an immunomodulatory protein.

7. The method of claim 6, wherein said immunomodulatory protein is selected from the group consisting of a cytokine, a chemokine, RANTES, a macrophage inflammatory peptide, a complement component or receptor, an immune system accessory molecules, an adhesion molecule, and an adhesion receptor molecule.

8. The method of claim 7, wherein said cytokine is selected from the group consisting of an interleukin, tumor necrosis factor, granulocyte macrophage colony stimulating factor (GM-CSF), macrophage colony stimulating factor (M-CSF), and granulocyte colony stimulating factor (G-CSF).

9. The method of claim 1, wherein said cancer of the nervous system is selected from the group consisting of astrocytoma, oligodendroglioma, meningioma, neurofibroma, glioblastoma, ependymoma, Schwannoma, neurofibrosarcoma, and neuroblastoma.

10. The method of claim 1, wherein said cancer of the nervous system is astrocytoma.

11. The method of claim 1, wherein said cancer of the nervous system is oligodendroglioma.

12. The method of claim 1, wherein said cancer of the nervous system is meningioma.

13. The method of claim 1, wherein said cancer of the nervous system is neurofibroma.

SEQUENCE LISTING

<160> NUMBER OF SEQ ID NOS: 1

<210> SEQ ID NO 1
<211> LENGTH: 28
<212> TYPE: DNA
<213> ORGANISM: Artificial Sequence
<220> FEATURE:
<223> OTHER INFORMATION: Synthetic Construct

<400> SEQUENCE: 1
gggccctgag ttgcccaatg gcctaaat                                    28

14. The method of claim 1, wherein said cancer of the nervous system is glioblastoma.

15. The method of claim 1, wherein said cancer of the nervous system is ependymoma.

16. The method of claim 1, wherein said cancer of the nervous system is Schwannoma.

17. The method of claim 1, wherein said cancer of the nervous system is neurofibrosarcoma.

18. The method of claim 1, wherein said cancer of the nervous system is neuroblastoma.

19. The method of claim 7, wherein said cytokine is granulocyte macrophage colony stimulating factor (GM-CSF).

\* \* \* \* \*